US011844696B2

(12) United States Patent
Justin et al.

(10) Patent No.: US 11,844,696 B2
(45) Date of Patent: Dec. 19, 2023

(54) MEDICAL IMPLANT SURFACE TREATMENT AND METHOD

(71) Applicant: Revision Technologies LLC, Orlando, FL (US)

(72) Inventors: Daniel F. Justin, Orlando, FL (US); James Q. Spitler, Ocoee, FL (US)

(73) Assignee: Revision Technologies LLC, Orlando, FL (US)

( * ) Notice: Subject to any disclaimer, the term of this patent is extended or adjusted under 35 U.S.C. 154(b) by 538 days.

(21) Appl. No.: 16/967,503

(22) PCT Filed: Feb. 5, 2019

(86) PCT No.: PCT/US2019/016697
§ 371 (c)(1),
(2) Date: Aug. 5, 2020

(87) PCT Pub. No.: WO2019/153010
PCT Pub. Date: Aug. 8, 2019

(65) Prior Publication Data
US 2021/0212835 A1    Jul. 15, 2021

Related U.S. Application Data

(60) Provisional application No. 62/626,479, filed on Feb. 5, 2018.

(51) Int. Cl.
*A61F 2/34* (2006.01)
*A61F 2/30* (2006.01)

(52) U.S. Cl.
CPC ............ *A61F 2/34* (2013.01); *A61F 2/30734* (2013.01); *A61F 2/30907* (2013.01);
(Continued)

(58) Field of Classification Search
CPC .... A61F 2/34; A61F 2/30734; A61F 2/30907; A61F 2002/30331; A61F 2002/30383;
(Continued)

(56) References Cited

U.S. PATENT DOCUMENTS

| 5,176,711 A | 1/1993 | Grimes |
| 5,871,548 A | 2/1999 | Sanders et al. |

(Continued)

FOREIGN PATENT DOCUMENTS

| FR | 2775586 | 6/2000 |
| WO | WO 1999/022672 | 5/1999 |

OTHER PUBLICATIONS

Supplementary European Search Report dated Sep. 23, 2021 for corresponding European Patent Application No. 197480361.

(Continued)

*Primary Examiner* — Brian A Dukert
(74) *Attorney, Agent, or Firm* — David Meibos; Maywood IP Law

(57) ABSTRACT

Medical implant surface treatments and methods are described. Such a surface treatment may provide an uneven texture that is configured to interlock with adjoining bone and/or an uneven texture on another implant, such as an augment for an acetabular cup for revision hip surgery. At least one of the uneven texture of the cup bone-facing surface and the uneven texture of the augment cup-facing surface may include a web of rods. The rods may be configured to interlock with each other when the two implants are urged together.

8 Claims, 20 Drawing Sheets

(52) U.S. Cl.
CPC ............... *A61F 2002/3092* (2013.01); *A61F 2002/30383* (2013.01); *A61F 2002/30736* (2013.01)

(58) Field of Classification Search
CPC .. A61F 2002/30387; A61F 2002/30899; A61F 2002/30736
See application file for complete search history.

(56) References Cited

U.S. PATENT DOCUMENTS

| | | | |
|---|---|---|---|
| 6,340,370 | B1 | 1/2002 | Willert et al. |
| 6,416,553 | B1 | 7/2002 | White et al. |
| 8,197,550 | B2 * | 6/2012 | Brown .................. A61F 2/34 623/22.32 |
| 8,506,643 | B2 | 8/2013 | Keefer et al. |
| 8,556,986 | B2 | 10/2013 | Haidukewych |
| 9,005,304 | B2 | 4/2015 | Haidukewych |
| 9,089,430 | B2 | 7/2015 | Pappas et al. |
| 10,588,755 | B2 * | 3/2020 | Vogt .................... A44B 18/0065 |
| 2005/0080487 | A1 * | 4/2005 | Schultz ................. A61F 2/4425 623/17.13 |
| 2008/0021568 | A1 | 1/2008 | Tulkis et al. |
| 2009/0204225 | A1 | 8/2009 | Meridew et al. |
| 2009/0326670 | A1 | 12/2009 | Keefer et al. |
| 2010/0004754 | A1 | 1/2010 | Brown et al. |
| 2012/0016485 | A1 | 1/2012 | Sharp |
| 2014/0180431 | A1 | 6/2014 | Conway et al. |
| 2019/0021862 | A1 * | 1/2019 | Kalpakci ............... A61F 2/2846 |
| 2019/0209329 | A1 | 7/2019 | Smith |

OTHER PUBLICATIONS

International Search Report and Written Opinion dated May 23, 2019 for corresponding International Application No. PCT/US2019/016697.

Wong, "3-D Printed Patient-Specific Applications in Orthopedics", *Orthopedic Research and Reviews*, Oct. 14, 2016:8, pp. 57-66.

* cited by examiner

MEDICAL IMPLANT SURFACE TREATMENT AND METHOD

CROSS-REFERENCE TO RELATED APPLICATIONS

This application is a U.S. national stage filing under 35 U.S.C. § 371 of International Application No. PCT/US2019/016697, filed on Feb. 5, 2019, which claims the benefit of U.S. Provisional Application No. 62/626,479, filed on Feb. 5, 2018. All of the foregoing are incorporated as though set forth herein in their entirety.

TECHNICAL FIELD

The present disclosure relates to surgical systems and methods. More specifically, the present disclosure relates to surface treatments and methods that help implants more securely bond to each other and/or to adjoining bone.

BACKGROUND

Joint arthroplasty procedures are surgical procedures in which one or more articulating surfaces of a joint are replaced with prosthetic articulating surfaces. Such procedures are becoming increasingly commonplace, particularly for the acetabular femoral joint, commonly known as the hip joint. An arthroplasty procedure for the acetabular femoral joint can include implanting an acetabular joint prosthesis to replace the articulating surfaces of the acetabulum. This may or may not be performed along with replacement of the articulating surfaces of the femoral head.

For a successful acetabular joint arthroplasty, it is important that the implants remain in place and maintain the necessary wear characteristics. Further, it is desirable for the acetabular joint arthroplasty procedure to be carried out quickly and smoothly. Many existing acetabular joint arthroplasty implants and methods are time-consuming to implant or do not form a sufficient attachment to the underlying bone. Further, many known surface treatments do not provide sufficient adherence to bone and/or adjoining implants.

SUMMARY

The various systems and methods of the present disclosure have been developed in response to the present state of the art, and in particular, in response to the problems and needs in the art that have not yet been fully solved by currently available medical implant surface treatments and methods. The systems and methods of the present disclosure may provide surface treatments and methods that can be used with a wide variety of implant types. Acetabular implants and instruments are described by way of example, including but not limited to prosthetic acetabular cups, augments, and augment-securing mechanisms, that provide enhanced bone fixation and/or streamlined implantation through the use of enhanced surface treatments.

According to some embodiments, an acetabular joint prosthesis may be designed to replace an acetabular articular surface on a pelvis. The prosthesis may include a prosthetic acetabular cup, which may include a cup bone-facing surface having a generally convex shape, and a cup joint-facing surface having a generally concave shape. The prosthesis may also include an augment, which can include an augment cup-facing surface that is securable to the cup bone-facing surface, and an augment bone-facing surface. The augment bone-facing surface can be configured to face a portion of a pelvis to which the cup is attached, with the augment cup-facing surface secured to the cup bone-facing surface. The prosthesis can also include an augment-securing mechanism configured to secure the augment to the cup with at least a portion of the cup bone-facing surface facing at least a portion of the augment cup-facing surface. The augment-securing mechanism can include a guide feature extending along one of the cup bone-facing surface and the augment cup-facing surface; and a slider on the other of the cup bone-facing surface and the augment cup-facing surface that engages the guide feature. The augment-securing mechanism can be reconfigurable between an unlocked configuration, in which the slider is slidable along the guide feature; and a locked configuration in which the slider and the guide feature are frictionally engaged such that the slider is fixed in place relative to the guide feature. The locked configuration can include at least one of the slider or the guide feature being in an expanded form relative to a non-expanded form in the unlocked configuration.

The locked configuration may include the slider being in the expanded form, relative to the non-expanded form in the unlocked configuration. For example, the guide feature can define a slot, and the slider can include a protrusion that is configured to extend into the slot. The slider can include a shoulder surface that is configured to engage a corresponding shoulder surface defining a portion of the slot. Engagement between the slider shoulder surface and the slot-defining shoulder surface can inhibit movement of the slider out of the slot. The slider may include a dovetail-shaped member that includes the shoulder surface.

The guide feature can extend along the cup bone-facing surface, and the slider can be on the augment cup-facing surface. The slider may be an integral part of the augment, and the guide feature may define a slot formed in the cup bone-facing surface. The guide feature may define a curved path of movement for the slider, which can generate a curved path of movement of the augment along a portion of the cup bone-facing surface.

In the unlocked configuration, the augment-securing mechanism may facilitate rotation of the augment relative to the cup, and in the locked configuration the augment-securing mechanism can inhibit rotation of the augment relative to the cup. Also, the augment-securing mechanism can include a fastener that is rotatable to cause a transformation between the expanded form and the non-expanded form.

In other embodiments, an acetabular joint prosthesis can be designed to replace an acetabular articular surface on a pelvis. The acetabular joint prosthesis can include a prosthetic acetabular cup, which can include a cup bone-facing surface having a generally convex shape, and a cup joint-facing surface having a generally concave shape. The joint prosthesis can also include an augment, which can include an augment cup-facing surface that is securable to the cup bone-facing surface, and an augment bone-facing surface. The joint prosthesis can also include an augment-securing mechanism can be configured to secure the augment to the cup with at least a portion of the cup bone-facing surface facing at least a portion of the augment cup-facing surface. The augment-securing mechanism can include a pair of members that are rotatable relative to each other. The augment-securing mechanism can be reconfigurable between an unlocked configuration and a locked configuration. In the unlocked configuration, the augment can be rotatable about an axis between multiple rotational positions relative to the cup. In each of the rotational positions, with the augment cup-facing surface secured to the cup bone-facing surface, the augment cup facing surface can be configured to face a portion of a pelvis to which the cup is attached. In the locked configuration, the augment can be fixed in place in one of the rotational positions. The augment-securing mechanism can be reconfigurable into the locked configuration with the augment in any of the multiple rotational positions.

In each of the rotational positions in the locked configuration, an area of the augment cup-facing surface may face a corresponding area of the cup-bone-facing surface and match a curvature of the corresponding area of the cup bone-facing surface. For example, the cup bone-facing surface and the augment cup-facing surface may have matching spherical curvatures.

In these embodiments, the augment-securing mechanism may include a guide feature extending along one of the cup bone-facing surface and the augment cup-facing surface, and a slider on the other of the cup bone-facing surface and the augment cup-facing surface that engages the guide feature. In the unlocked configuration, the slider may be slidable along the guide feature, and in the locked configuration the slider and the guide feature may be frictionally engaged such that the slider is fixed in place relative to the guide feature.

The cup bone-facing surface may include an uneven texture that is configured to interlock with an uneven texture of the augment cup-facing surface with the augment-securing mechanism in the locked configuration. For example, at least one of the uneven texture of the cup bone-facing surface and the uneven texture of the augment cup-facing surface can include a web of rods.

In other embodiments, a method can be directed to replacing an acetabular articular surface on a pelvis with an acetabular joint prosthesis. The method can include positioning a prosthetic acetabular cup in an acetabulum of a pelvis, with a generally convex shaped cup bone-facing surface of the acetabular cup facing the acetabulum and with a generally concave shaped cup joint-facing surface of the acetabular cup facing opposite the cup bone-facing surface. The cup joint-facing surface can define a rim proximate a plane. An augment can be moved relative to the cup to a position wherein an augment cup-facing surface of the augment faces the cup bone-facing surface and an augment bone-facing surface of the augment faces a portion of the pelvis. An augment-securing mechanism can be actuated to secure the augment to the cup in the position. This actuating can include moving an instrument toward the acetabular cup in an access direction generally perpendicular to the plane to engage a securing area of the augment-securing mechanism.

The actuating of the augment-securing mechanism can include using the instrument to rotate a fastener around an axis that is generally perpendicular to the plane. Also, the actuating of the augment-securing mechanism may include using the instrument to move a fastener in a direction that is generally perpendicular to the plane.

The augment-securing mechanism may include a guide feature extending along one of the cup bone-facing surface and the augment cup-facing surface, and a slider on the other of the cup bone-facing surface and the augment cup-facing surface that engages the guide feature. The actuating of the augment-securing mechanism can include reconfiguring the augment-securing mechanism from an unlocked configuration, in which the slider is slidable along the guide feature, to a locked configuration in which the slider and the guide feature are frictionally engaged such that the slider is fixed in place relative to the guide feature.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the figures herein, could be arranged and designed in a wide variety of different configurations. Thus, the following more detailed description of the embodiments of the apparatus, system, and method, as represented in the figures, is not intended to limit the scope of the claims, as claimed, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
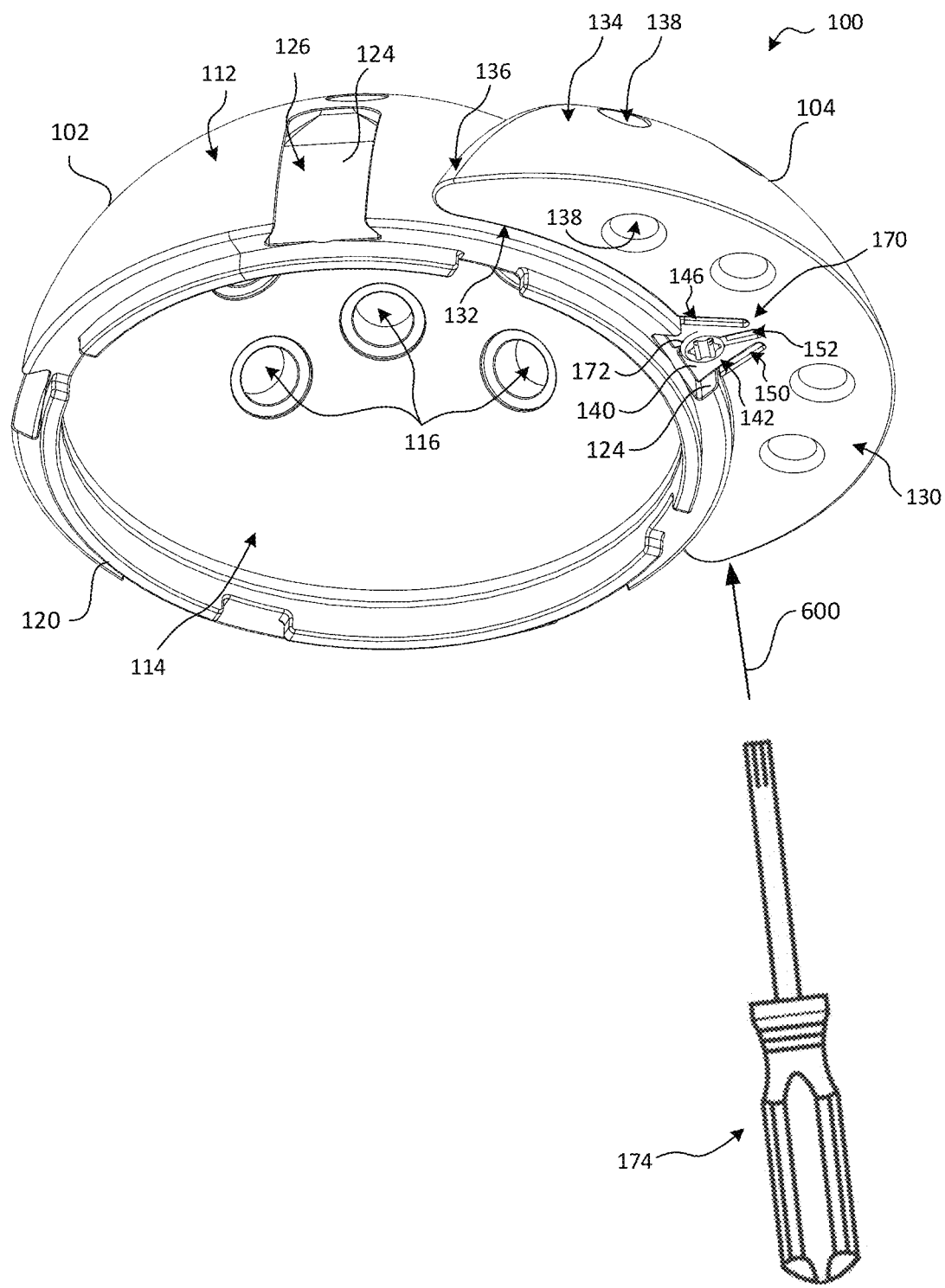
FIG. 1 is a perspective view of an acetabular joint prosthesis according to an embodiment.
Figure 2A:
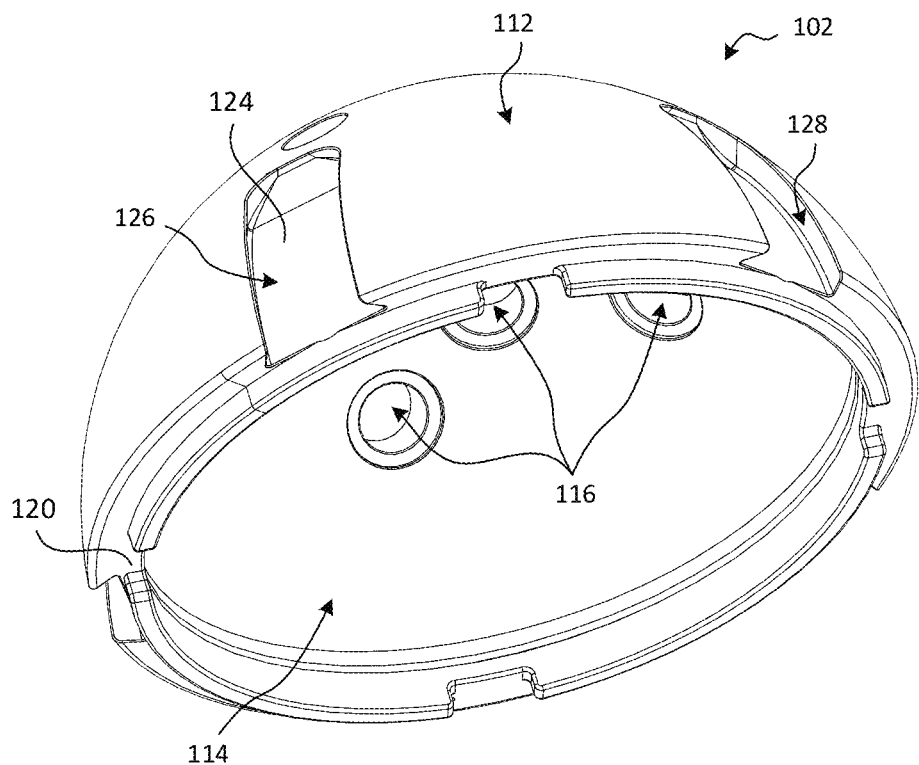
FIG. 2A is a perspective view of an acetabular cup of the acetabular joint prosthesis of FIG. 1.
Figure 2B:
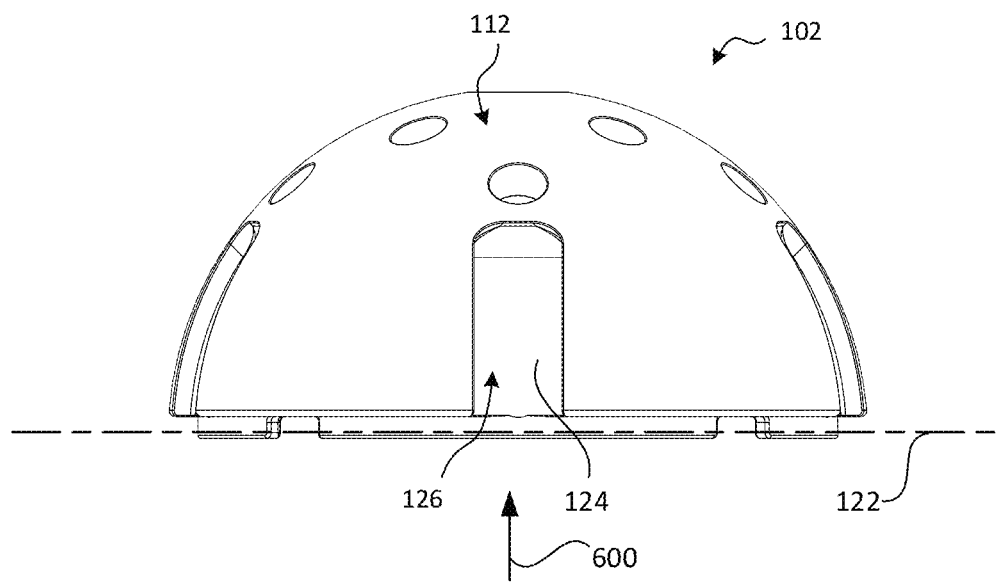
FIGS. 2B-2D are front, top, and bottom views, respectively, of the acetabular cup of FIG. 2A. As used herein, the directional terms front, back, left, right, top, and bottom, when referring to the components of the acetabular joint prosthesis, are used for convenience in describing the embodiments of the acetabular joint prosthesis. When used as such, it should be appreciated that they do not refer to orientation directions relative to a human body when the joint prosthesis is implanted in an acetabular joint, and they should not be construed as limiting the orientation relative to the pelvis when the acetabular joint prosthesis is implanted.
Figure 2C:
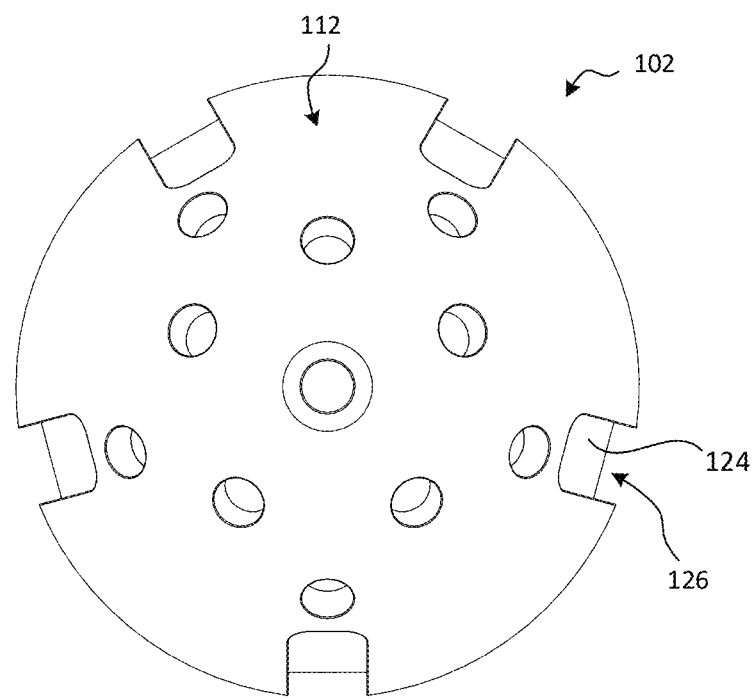
Figure 2D:
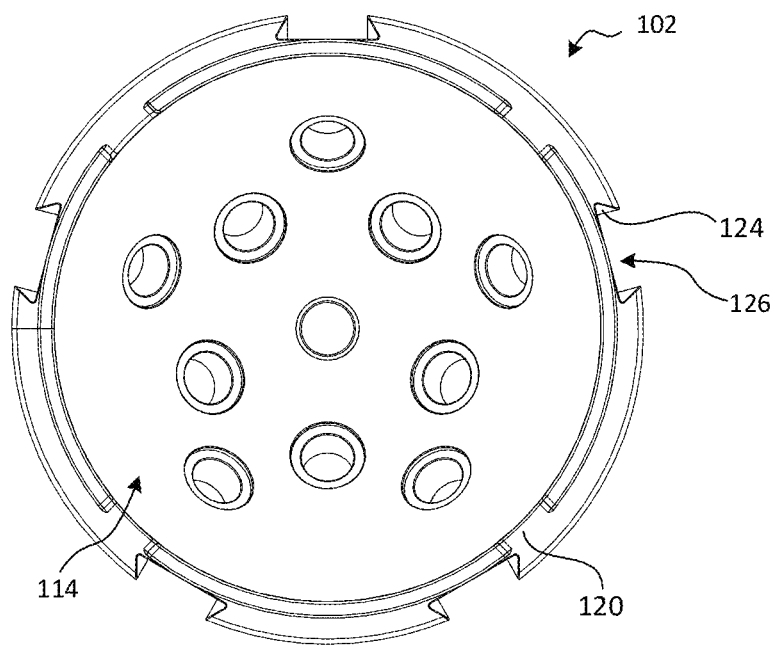
Figure 3A:
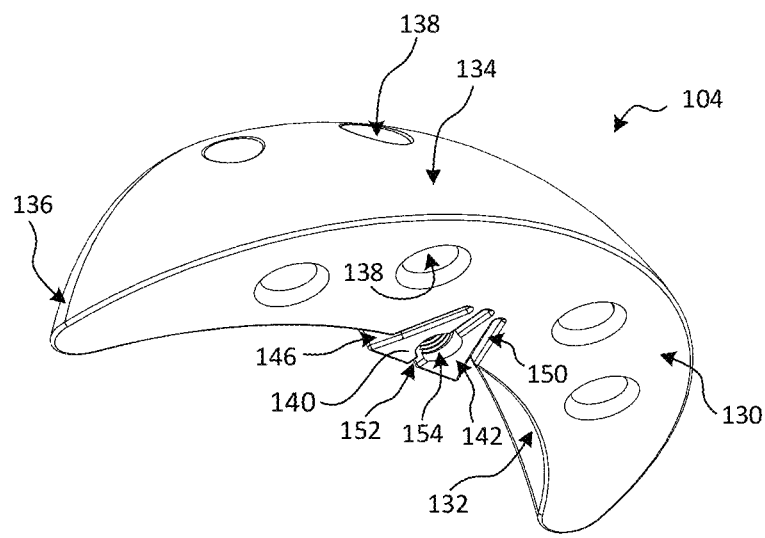
FIG. 3A is a perspective view of an augment of the acetabular joint prosthesis of FIG. 1.
Figure 3B:
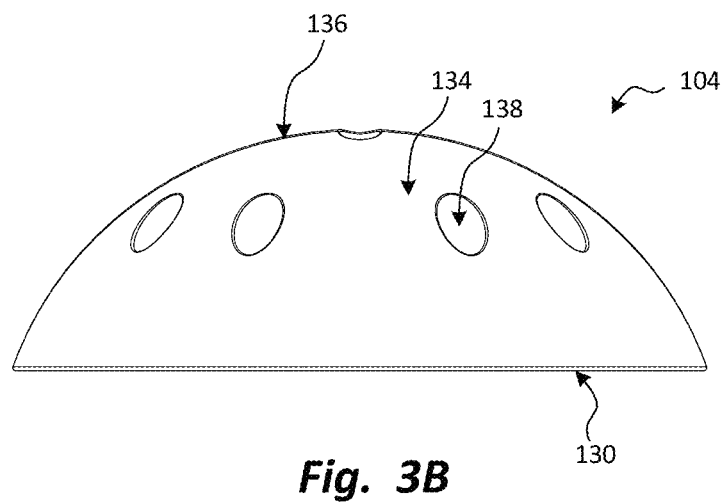
FIGS. 3B-3G are front, back, top, bottom, left, and right views, respectively, of the augment of FIG. 3A.
Figure 3C:
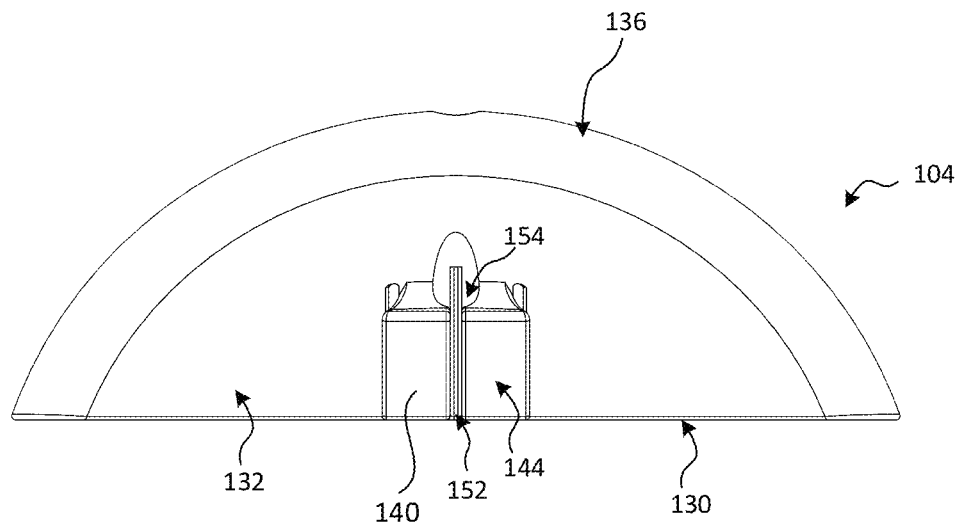
Figure 3D:
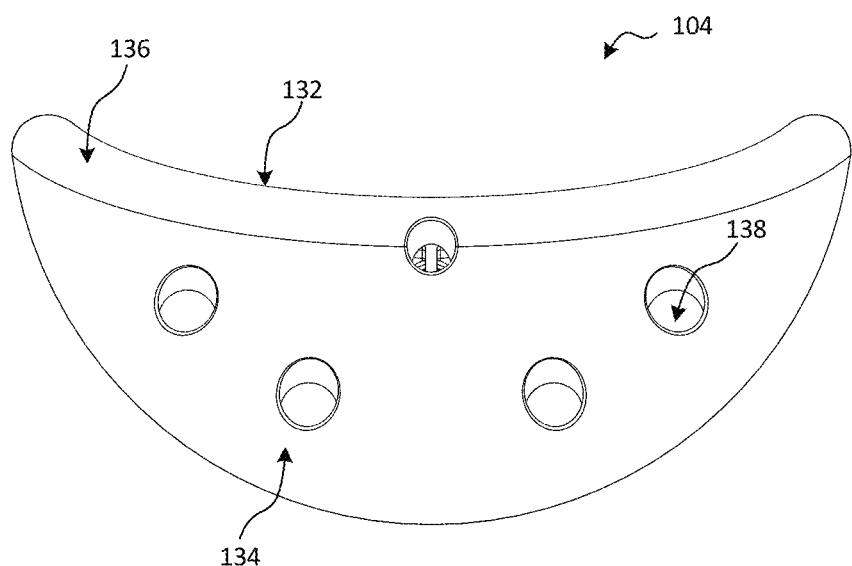
Figure 3E:
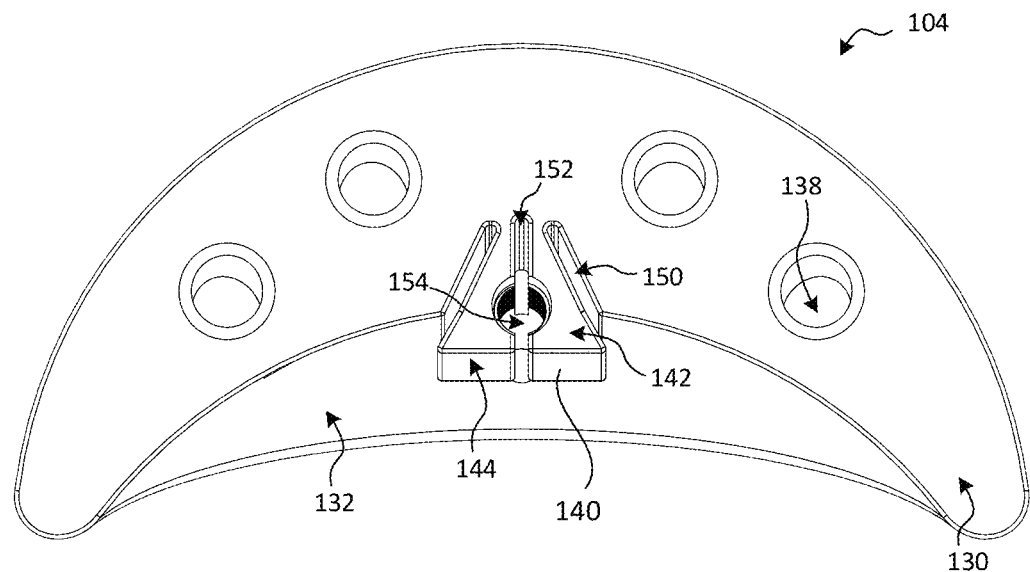
Figures 3F, 3G:
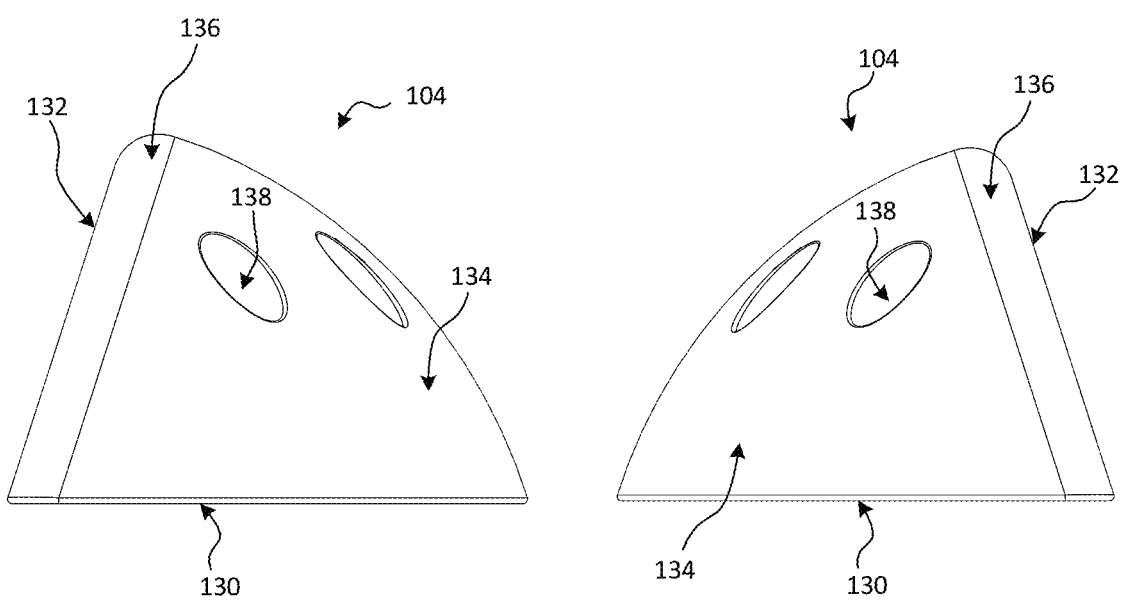

FIG. 1 is a perspective view of an acetabular joint prosthesis 100, according to one embodiment. The joint prosthesis 100 may be designed to replace the natural or previously-implanted artificial articulating surfaces of the acetabulum, which may receive and operate in conjunction with natural or prosthetic articulating surfaces of the femoral head (not shown). The prosthesis 100 may be particularly well suited for replacing an existing prosthetic acetabular cup, such as where the cup has become dislodged and/or bone decay has occurred around the cup. In particular, the augments discussed herein can assist in securing a prosthetic acetabular cup in such situations, such as by providing a greater area in which to secure the prosthesis to the pelvis. For example, this can be done by allowing the bone to grow into and/or around the augment, and allowing for additional opportunities to fix the prosthesis in place using screws, some of which can extend through the augment and into the pelvis.

The prosthesis 100 can include an acetabular cup 102 and at least one augment 104. Referring to FIGS. 2A-2D, the cup 102 can be a generally hollowed shell, such as a hollowed generally hemispherical shape. The acetabular cup 102 can include a cup bone-facing surface 112 that can be generally convex in all directions and a cup joint-facing surface 114 that can be generally concave in all directions. However, each surface may include localized portions that do not conform to the general convex or concave curvature of the surface. For example, this may be the case where the surface includes an uneven texture, as discussed below. The cup bone-facing surface 112 can be generally shaped to fit in a prepared acetabulum. The cup joint-facing surface 114 can be shaped fit around articulating surfaces of a natural or prosthetic femur head.

The cup 102 can define one or more apertures, such as holes 116. The holes 116 can pass through the cup 102 from the cup joint-facing surface to the cup bone-facing surface. For example, in the embodiment of FIGS. 2A-2D, the holes 116 can include a centrally located hole, a first set of 5 holes spaced in a circular pattern centered around the centrally located hole, and a second set of 5 holes spaced in a circular pattern centered around the centrally located hole farther from the central hole than the first set. However, the holes 116 could be in various other different patterns, numbers, and/or sizes. The holes 116 can facilitate securing of the cup to the adjacent pelvic bone. For example, one or more of the holes 116 can receive a screw or other fastener, which can extend through the hole 116 and into the bone of the pelvis. Also, as the cup 102 remains seated in the acetabulum over time, the bone of the acetabulum can grow into the holes 116 to help the cup 102 be even more securely fixed in the acetabulum.

The cup 102 can also include a rim 120, which can be generally circular in an embodiment where the cup 102 is a generally hemispherical shape. The rim 120 can be proximate a plane 122 (see FIG. 2B). As used herein, for a rim to be proximate to a plane means for the plane to be aligned with the rim, if the rim is planar. However, if the rim is not planar, then a plane is proximate to the rim if the plane is positioned to minimize the summed perpendicular distance from the plane to points around the rim.

The cup 102 can also include guide features 124, each of which can define a slot 126 that extends into the cup 102 from the cup bone-facing surface 112. The cup 102 defines five such guide features 124 spaced around the cup 102, with each guide feature 124 defining a slot 126 extending from the rim 120 along the cup bone-facing surface 112 toward the center of the cup 102 (i.e., toward the central location of the central hole). Each slot 126 can extend along the cup bone-facing surface 112 toward the center of the cup 102 in a curved path, such as a path that matches the curvature of the cup bone-facing surface 112. Also, each slot 126 can become wider as it extends deeper into the cup 102 from the general cup bone-facing surface 112. Thus, the cup 102 can include, for each slot 126, a shoulder surface 128 (see FIG. 2A) of the corresponding guide feature 124 that defines the wider and deeper portion of the slot. In the embodiment illustrated in FIGS. 2A-2D, each slot 126 flares outward as it extends deeper into the cup 102, so that each slot has a generally trapezoidal-shaped (i.e., dovetail-shaped) cross-section that is narrower at the surface and wider as it extends deeper into the cup 102.

Referring now to FIGS. 3A-3G, the augment 104 will be discussed in more detail. The augment 104 can include a generally planar augment flesh-facing surface 130 that is configured to face generally away from a pelvis and toward surrounding flesh when the joint prosthesis 100 is implanted (although the augment may be oriented so that the augment flesh-facing surface 130 faces some portion of the pelvis). The augment can also include an augment cup-facing surface 132 that is configured to face the cup bone-facing surface 112 of the cup 102 (see FIG. 1), and an augment bone-facing surface 134 that is configured to generally face toward a pelvis when the joint prosthesis 100 is implanted. The augment cup-facing surface 132 can have a concave curvature in all directions that matches the convex curvature of the cup bone-facing surface 112. For example, such curvature may be a spherical curvature. In the augment illustrated in FIGS. 3A-3G, the augment flesh-facing surface 130 is generally crescent shape with rounded tips. The augment cup-facing surface 132 can be generally concave in all directions to match the cup bone-facing surface 112 of the cup 102. The augment bone-facing surface 134 can be generally convex in all directions.

The augment cup-facing surface 132 can extend from the concave edge of the augment flesh-facing surface 130, and the augment bone-facing surface 134 can extend from the convex edge of the augment flesh-facing surface 130. Also, the augment bone-facing surface 134 and the augment cup-facing surface 132 can meet each other to form a ridge 136 that extends in a convex arcuate path from one tip of the crescent-shaped flesh-facing surface 130 to the other tip of the crescent-shaped flesh-facing surface 130. The augment 104 can define holes 138 therein that extend from the flesh-facing surface 130 to the bone-facing surface 134. As with the holes 116 in the cup 102, the holes 138 in the augment 104 can receive one or more screws for securing the augment to the pelvis. Also, the holes 138 can allow bone growth therein over time to aid in securing the augment 104 to the pelvis, and thereby assist in securing the cup 102 to the pelvis. While the overall shape of the augment 104 is described here in detail, as is discussed more below, augments can have many different shapes.

The augment 104 can further include a slider 140, which can be integrally formed with the remainder of the augment 104. The slider 140 can be centrally located proximate the concave edge of the crescent-shaped flesh-facing surface 130. The slider 140 can include a planar surface 142 that is co-planar with the flesh-facing surface 130. Additionally, the slider can include an end surface 144 that faces away from the main body of the augment 104 (facing substantially the same direction as the adjacent cup-facing surface 132 of the augment 104, though the end surface 144 can be planar instead of concave). Additionally, the slider 140 can include opposing side surfaces 146, or shoulder surfaces, that extend from the end surface back to the main body of the augment 104. The slider 140 can extend from the augment flesh-facing surface 130 along the augment cup-facing surface 132. Also, the slider 140 can widen as it extends out and away from the augment cup-facing surface 132. In the specific embodiment illustrated in FIGS. 3A-3G, the slider can form a general dovetail shape that matches the dovetail shape of the slots 126 in the cup 102. Thus, the side surfaces 146 of the slider 140 can face and engage the shoulder surfaces of the corresponding guide feature 124 of the cup 102 to inhibit movement of the slider 140 out of a slot 126 in which the slider 140 is seated. The slider 140 can also extend into the body of the augment 104, with the augment 104 forming side slots 150 on each side of the slider 140, between the side surfaces 146 of the slider 140 and the main body of the augment 104. Additionally, the slider 140 can define a center slot 152 that extends into the slider 140, between the side slots 150. The slider 140 can also define an aperture 154, such as a threaded hole that extends into the slider 140 from the planar surface 142, so that the center slot 152 extends on opposite sides of the aperture 154.

Referring back to FIG. 1, parts of the cup 102 and the augment 104 can also be part of an augment-securing mechanism 170, which can also include additional components. That mechanism 170 can be reconfigured between a locked configuration in which the augment 104 can be fixed relative to the cup 102, and an unlocked configuration in which the augment-securing mechanism 170 facilitates movement between the augment 104 and the cup 102. In the embodiment illustrated in FIG. 1, the augment-securing mechanism can include the slider 140, a corresponding guide feature 124 defining a slot 126 in which the slider 140 is seated, and a fastener 172 that is moveable to expand the slider 140. For example, the fastener 172 can be a screw that is able to be screwed into the aperture 154 in the slider 140. At least a portion of the aperture 154 can be smaller than the fastener 172, so that as the fastener 172 extends into the aperture 154, the fastener 172 forces portions of the slider 140 on opposite sides of the aperture 154 and center slot 152 to spread apart, thereby expanding the slider. This reconfiguration of the slider 140 from a non-expanded form to an expanded form can produce friction between the slider 140 and the corresponding guide feature 124 that defines the corresponding slot 126. This friction can lock or fix the slider 140 in place relative to the guide feature 124, which can fix the augment 104 in place relative to the cup 102. Accordingly, the securing mechanism 170 can be reconfigured between a locked configuration and an unlocked configuration by moving the fastener 172 farther into the aperture 154 in the slider 140 for the locked configuration, and moving the fastener 172 farther out of the aperture 154 for the unlocked configuration. For example, where the fastener 172 is a screw, the fastener can be moved by rotating the fastener 172 about an axis. This can be performed using an instrument 174, such as a bit driver.

Figure 4:
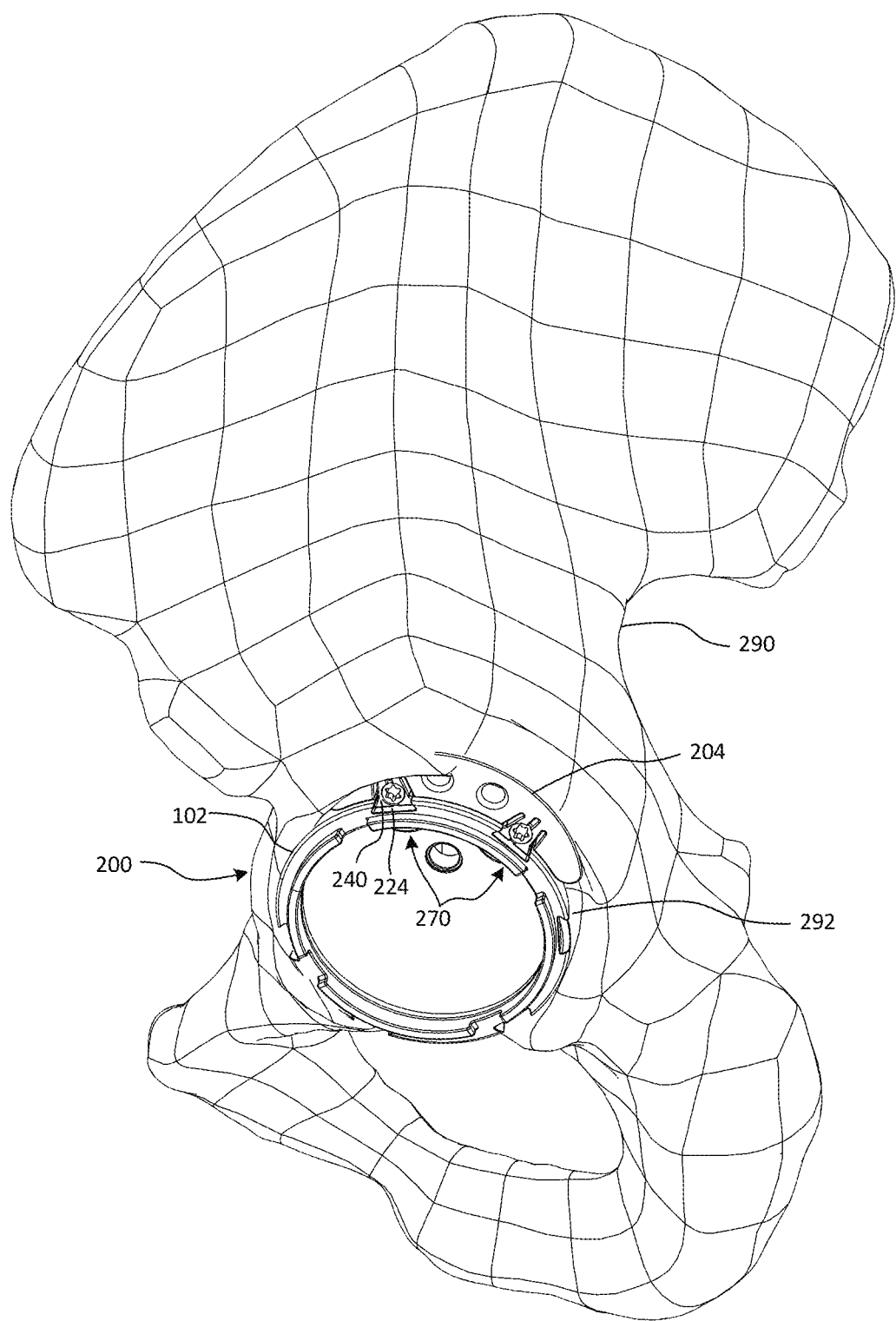
FIG. 4 is a view, from the left side of a pelvis, of an acetabular joint prosthesis implanted in an acetabulum of the pelvis.

Referring now to FIG. 4, another embodiment of a joint prosthesis 200 is illustrated. The joint prosthesis 200 can include the cup 102, an augment 204, and an augment-securing mechanism 270. All these components can be the same as in the joint prosthesis 100, except that the augment 204 and the augment-securing mechanism 270 can include multiple sliders 240 that interact with multiple guide features 224 for releasably securing a single augment 204. Also, FIG. 4 illustrates the joint prosthesis 200 implanted in a pelvis 290, and specifically in an acetabulum 292 of the pelvis 290.

Figure 5:
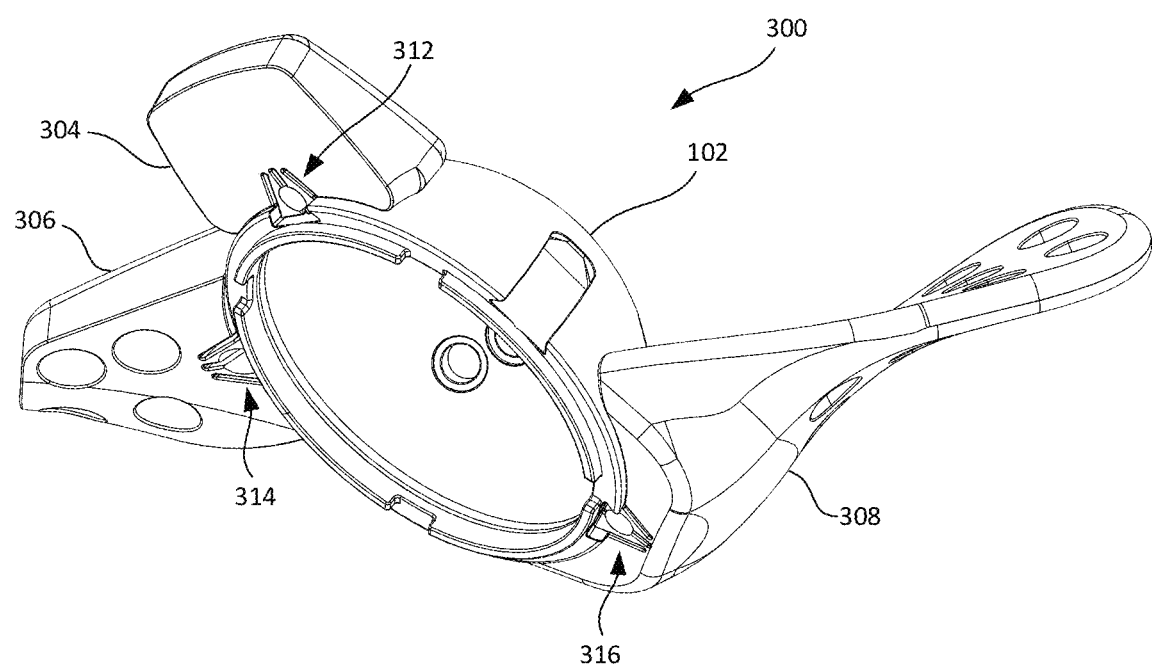
FIG. 5 is a perspective view of an acetabular joint prosthesis according to an embodiment.

A joint prosthesis may include different numbers of augments, and the augments may be different shapes to fit with different parts of a pelvis. Also, different shapes may be used for areas where there is bone decay, so that the augments can fit into decayed areas of the pelvis around the acetabulum. Referring now to FIG. 5, a joint prosthesis 300 is shown with the acetabular cup 102 and three different shaped augments 304, 306, and 308. The joint prosthesis includes three augment-securing mechanisms 312, 314, and 316, with one for each of the three augments 304, 306, and 308. Fasteners for the augment-securing mechanisms 312, 314, and 316 are not shown in FIG. 5, but fasteners may be included in the augment-securing mechanisms 312, 314, and 316. The augment-securing mechanisms 312, 314, and 316 can each be similar to the augment-securing mechanism 170 described above with reference to FIGS. 1-3G.

Figure 6A:
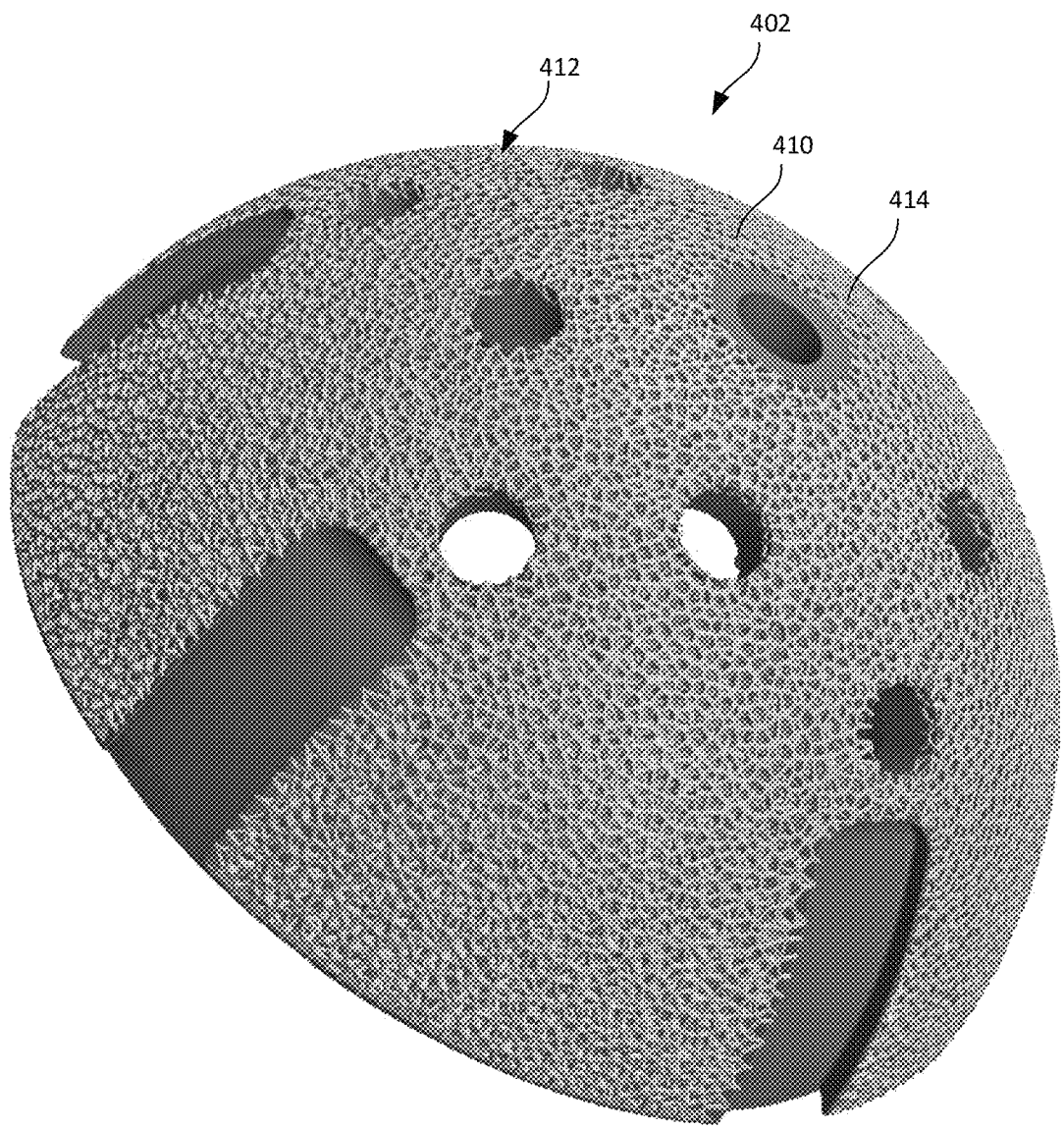
FIGS. 6A-6B are perspective views of an acetabular cup like the acetabular cup of FIGS. 2A-2D, but with added texture on a bone-facing surface of the cup.
Figure 6B:
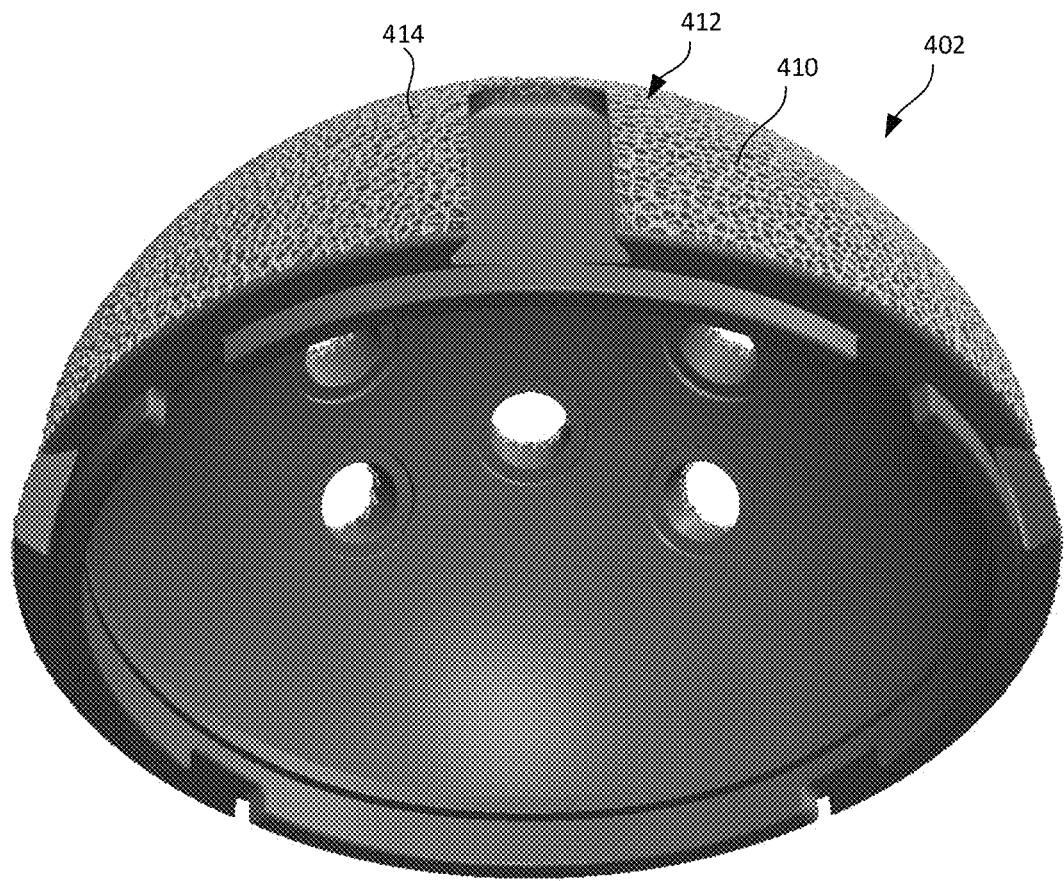
Figure 6C:
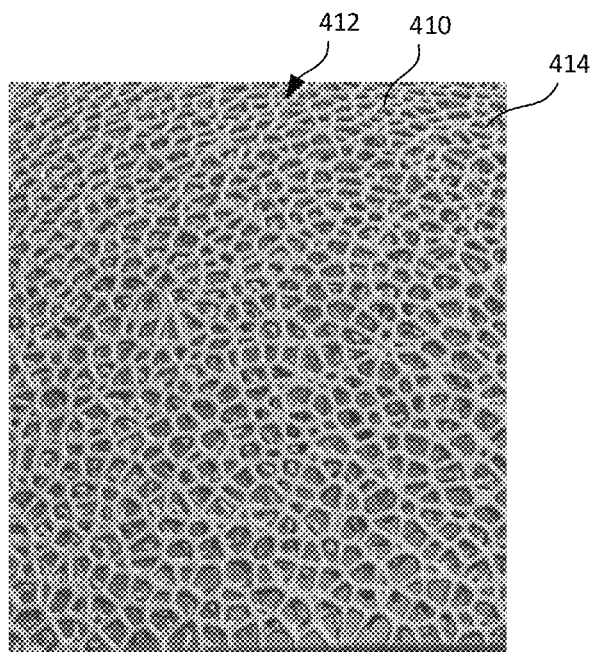
FIG. 6C is an enlarged cut-away view of a portion of the texture on the bone-facing surface of the cup of FIGS. 6A-6B.

Referring now to FIGS. 6A-7C, texture on an acetabular joint prosthesis will be discussed. An uneven texture, such as rough, raised, and/or pitted texture can help in securing the augment to the cup, and in securing the augment and the cup to the pelvis. Referring to FIGS. 6A-6C, an acetabular cup 402 similar to the acetabular cup 102 discussed above can include a generally convex cup bone-facing surface 412, which can include texture features 410 thereon. The texture features 410 can produce an uneven porous texture on the cup bone-facing surface 412, as opposed to the smoother texture of the cup bone-facing surface 112 discussed above. The texture features 410 can include a web of rods 414 extending along the surface. In one embodiment, the web of rods 414 can form a generally stochastic pattern as shown in FIGS. 6A-6C, or they may be in some other type of pattern, such as a repeated regular pattern.

Figure 7A:
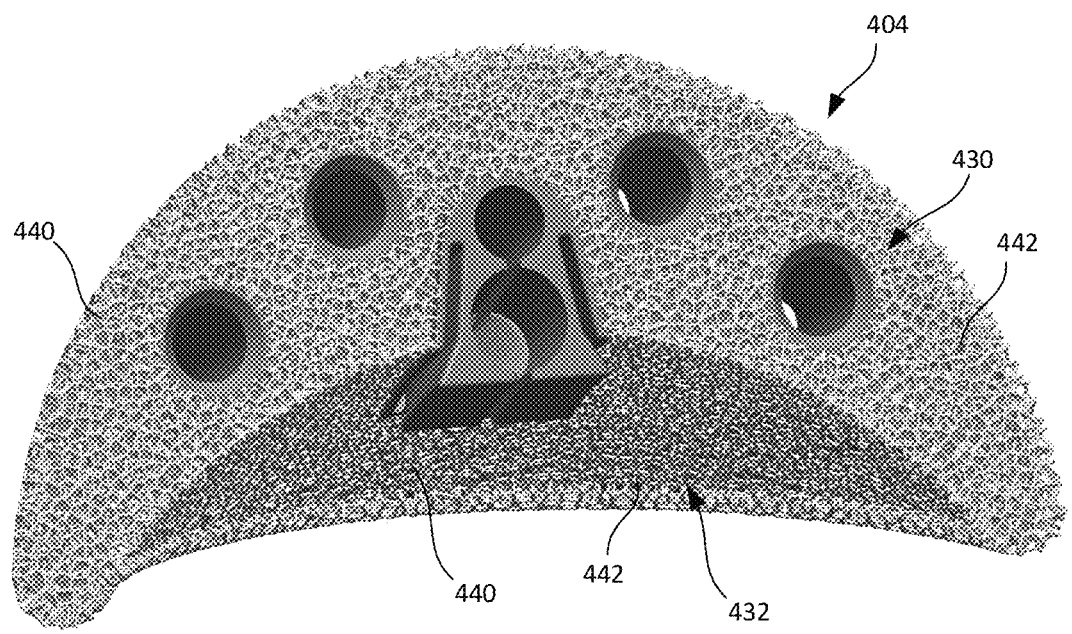
FIGS. 7A-7B are perspective views of an augment like the augment of FIGS. 3A-3G, but with added texture on the bone-facing, joint-facing, and cup-facing surfaces.
Figure 7B:
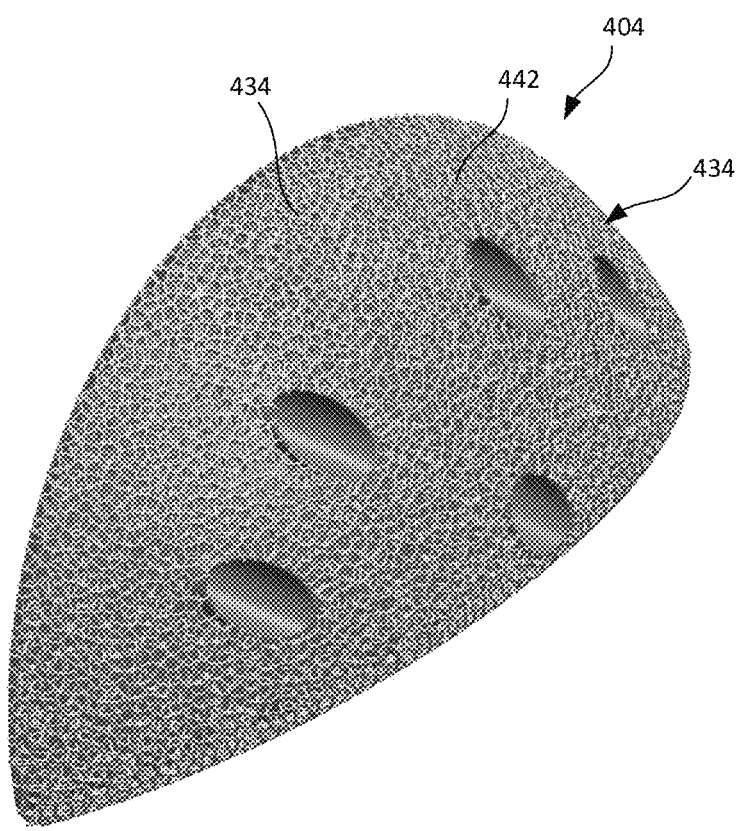
Figure 7C:
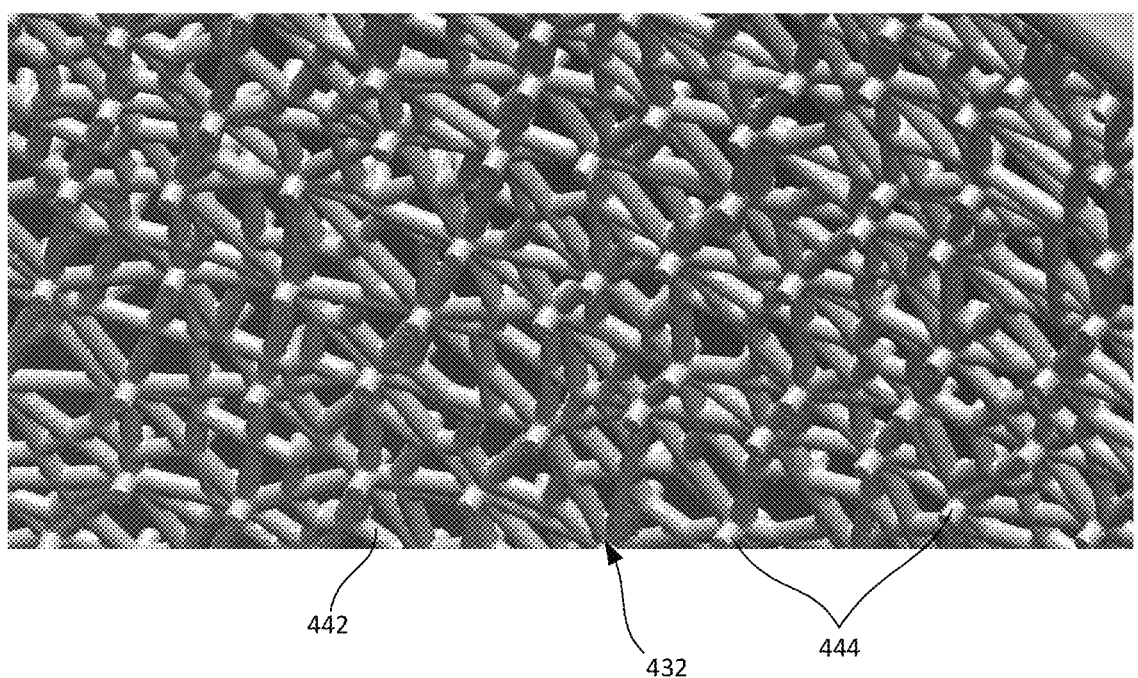
FIG. 7C is an enlarged cut-away view of a portion of the texture on the cup-facing surface of the augment of FIGS. 7A-7B.

Referring to FIG. 7A-7B, an augment 404 similar to the augment 104 discussed above can include a flesh-facing surface 430, a cup-facing surface 432, and a bone-facing surface 434, which can all include texture features 440 thereon. For example, each of the surfaces 430, 432, and 434 can include a web of rods 442 extending along the surfaces 430, 432, and 434. Additionally, the augment cup-facing surface 432 can include protrusions 444 (such as protruding rods), which can extend away from the augment cup-facing surface 432, and can terminate at a distal end away from the augment cup-facing surface 432. For example, a protrusion 444 may extend substantially perpendicular to the augment cup-facing surface 432 at the location of the protrusion 444. For example, the protrusions may extend from intersections of rods in the web of rods 442 on the augment cup-facing surface 432.

When the augment cup-facing surface 432 is pressed against the cup bone-facing surface 412, the protrusions 444 on the augment cup-facing surface 432 can extend into the web of rods 442 on the cup bone-facing surface 412. This can interlock the augment cup-facing surface 432 with the cup bone-facing surface 412, which can inhibit movement of the cup 402 relative to the augment 404, when the augment-securing mechanism is in a locked configuration so that the augment cup-facing surface 432 and the cup bone-facing surface 412 are pressed against each other. The protrusions may be formed on the cup bone-facing surface 412 instead of, or in addition to, the augment cup-facing surface 432. Also, the protrusions may be different shapes, so long as they protrude into corresponding uneven texture on a facing surface. Also, the texture features discussed here can be used on any of the different embodiments discussed herein, such as the joint prosthesis of FIG. 5 and the joint prosthesis of FIGS. 8-11G.

Figure 8:
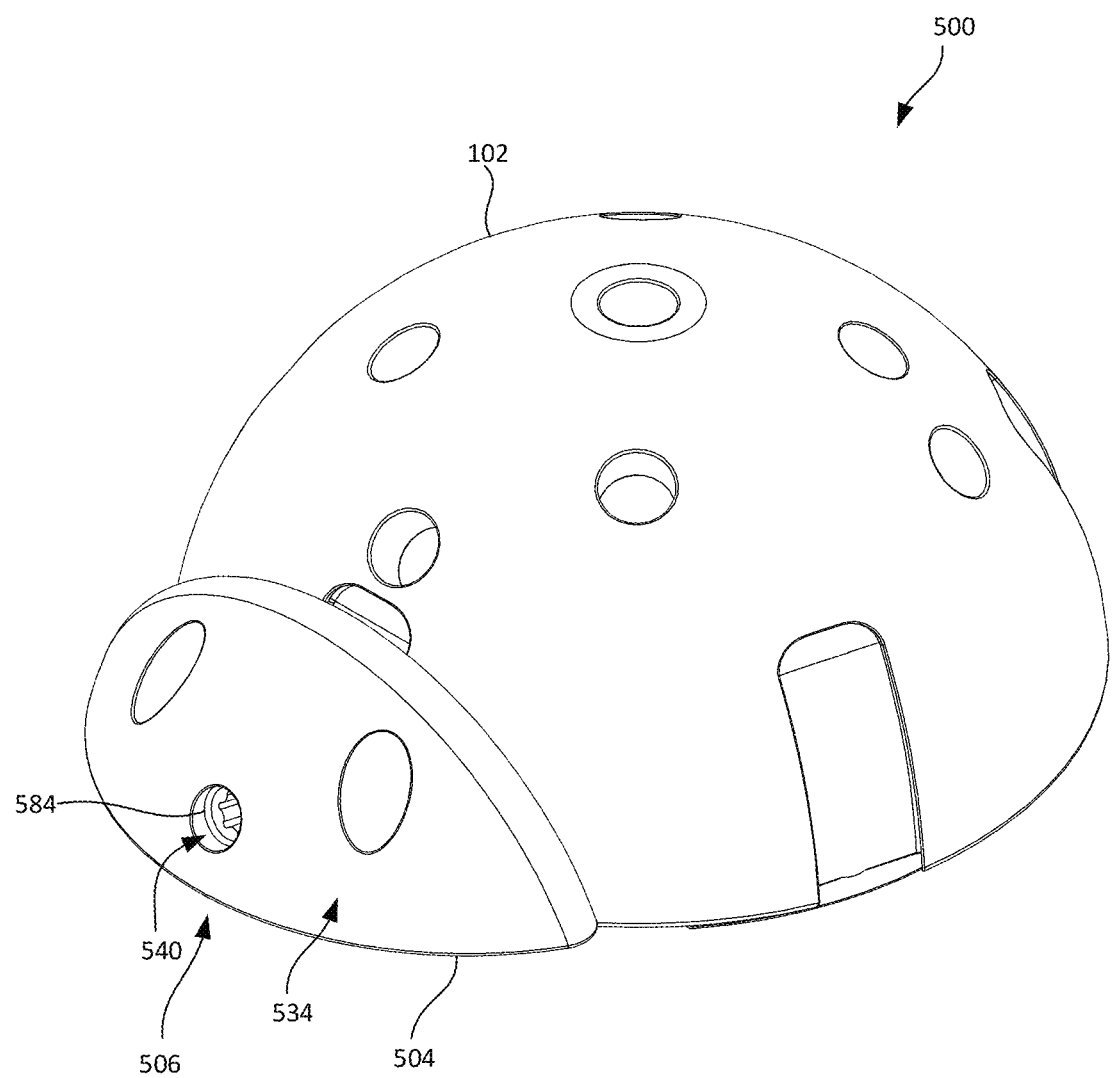
FIG. 8 is a perspective view of another embodiment of an acetabular joint prosthesis.
Figure 9:
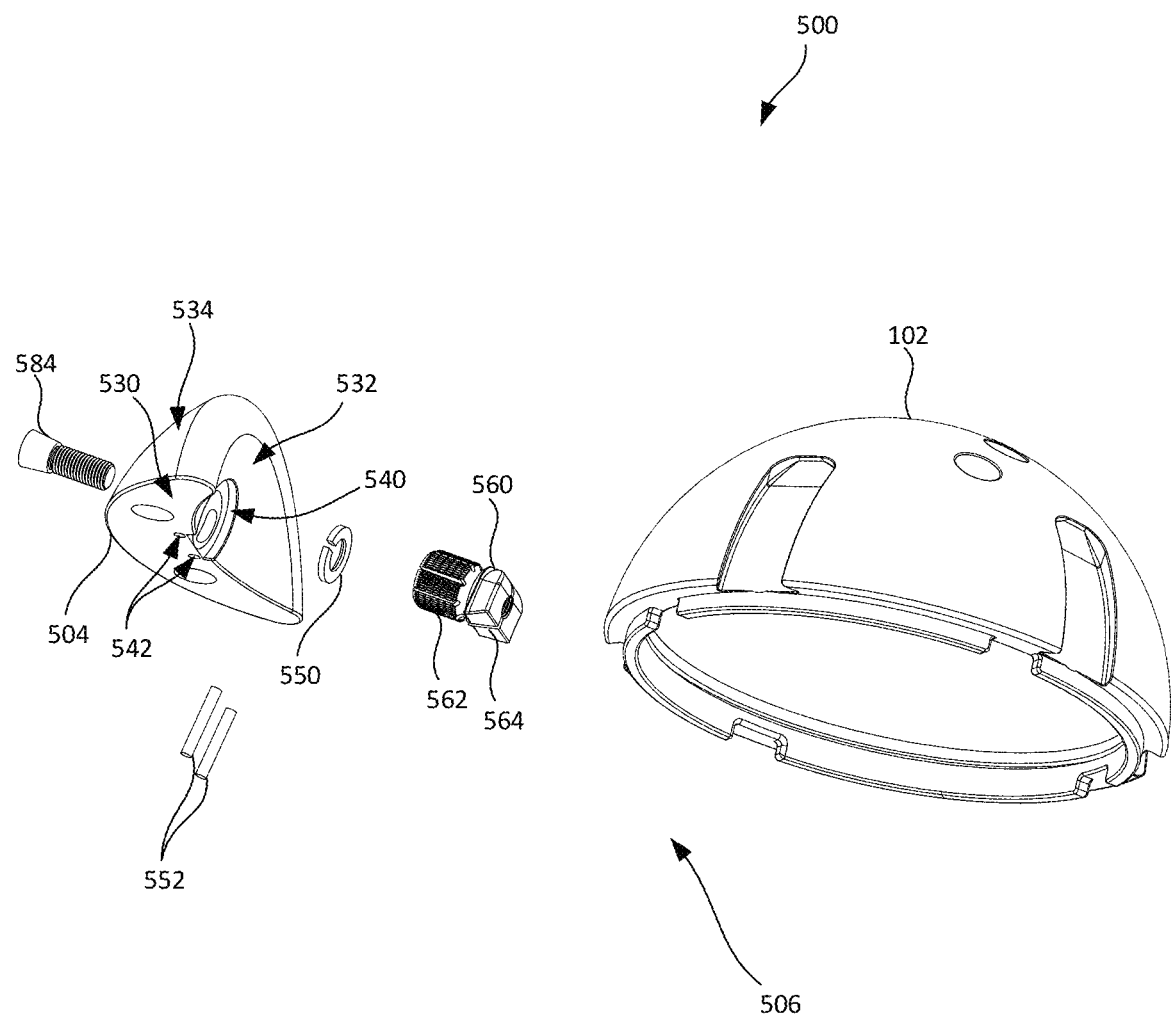
FIG. 9 is an exploded perspective view of the acetabular joint prosthesis of FIG. 8.

Another joint prosthesis 500 will now be discussed with reference to FIGS. 8-11G. Referring first to FIGS. 8-9, FIG. 8 is an assembled view of the joint prosthesis 500, and FIG. 9 is an exploded view of the joint prosthesis 500. The joint prosthesis 500 can be similar to the joint prosthesis 100. Indeed, in the joint prosthesis 500, the cup 102 can be the same as the cup 102 discussed above. However, augment 504 and the augment-securing mechanism 506 can be different from those described above. In general, the augment-securing mechanism 506 has an alternate structure that allows the cup 102 and the augment 504 to be rotated relative to each other in an unlocked configuration, and to be secured together in a fixed position with the augment 504 in any of multiple different rotational positions relative to the cup 102.

Figure 10A:
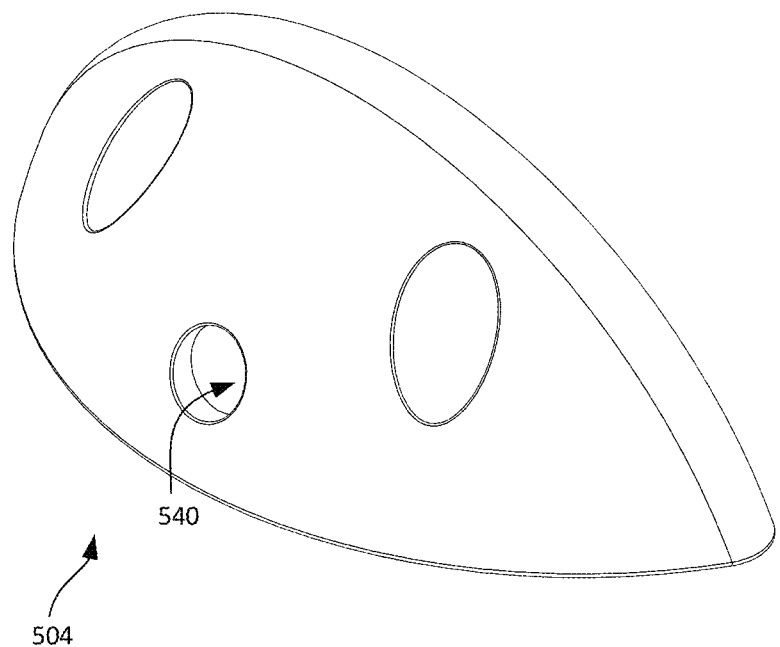
FIG. 10A is a perspective view of an augment of the acetabular joint prosthesis of FIG. 8.
Figure 10B:
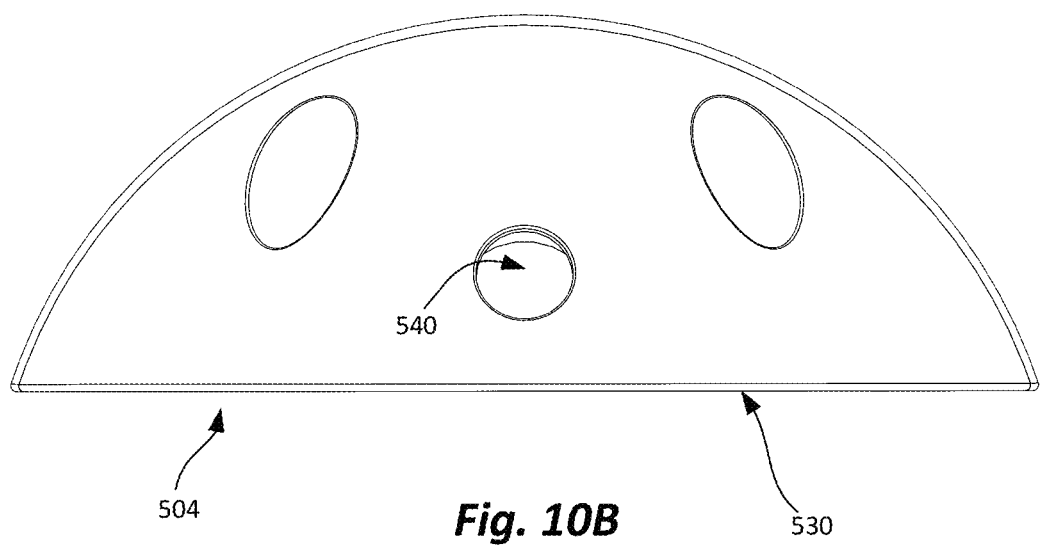
FIGS. 10B-10C are front and back views, respectively, of the augment of FIG. 10A.
Figure 10C:
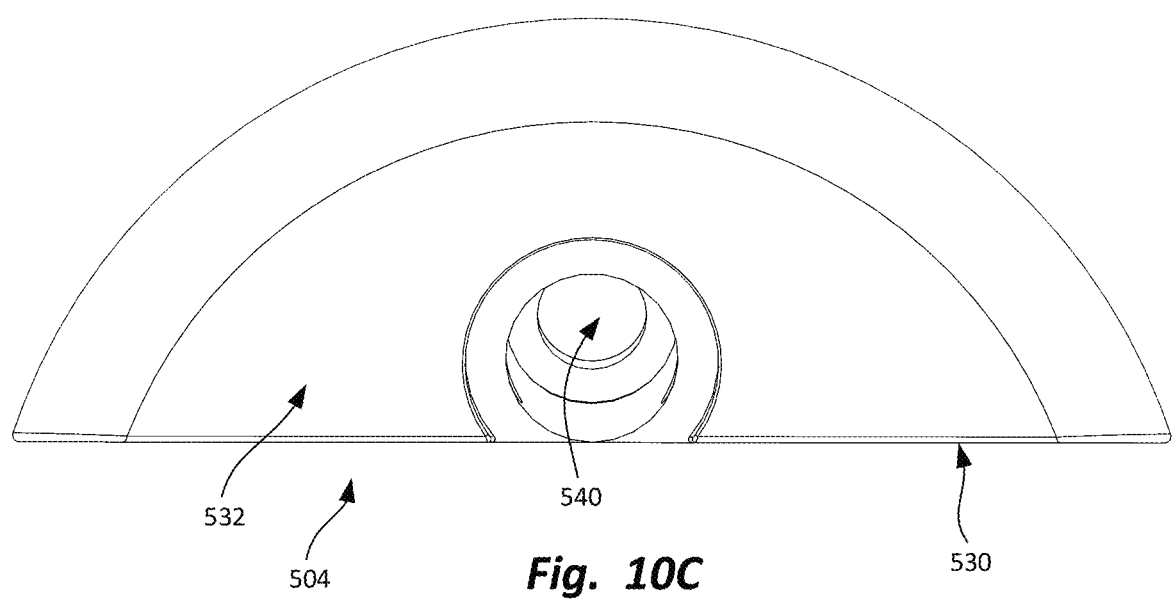
Figure 11A:
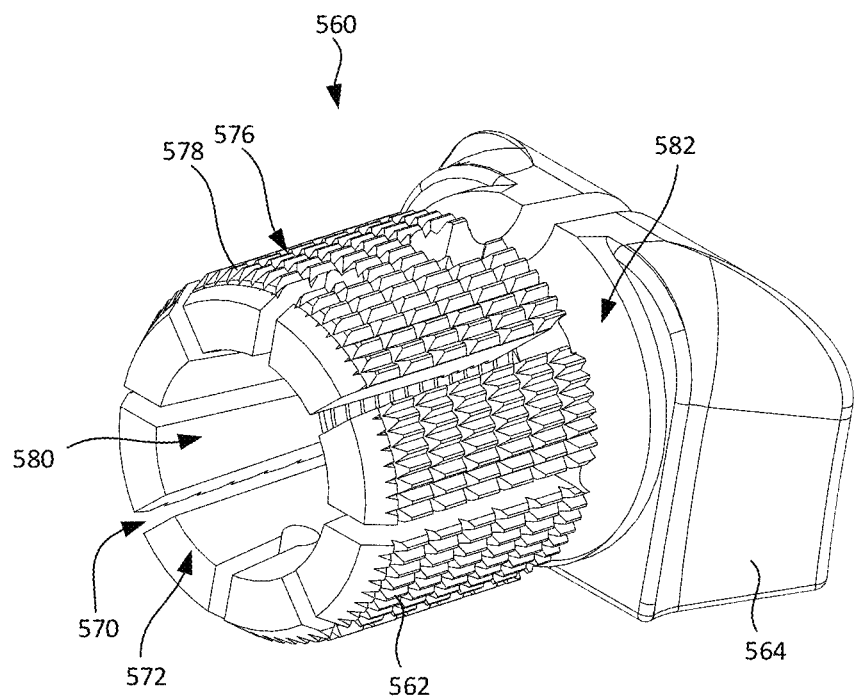
FIG. 11A is a perspective view of a saddle of the acetabular joint prosthesis of FIG. 8.
Figure 11B:
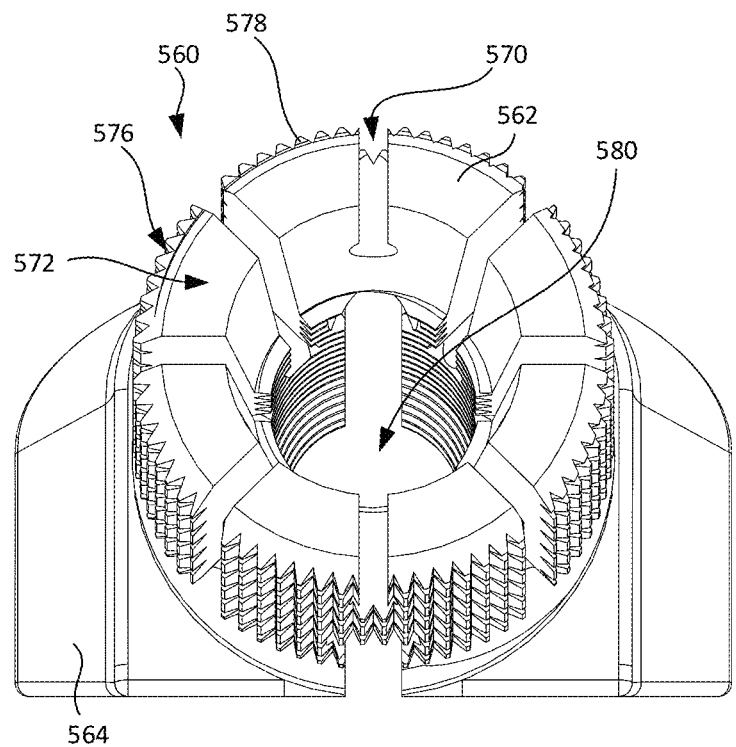
FIGS. 11B-11G are front, back, top, bottom, left, and right views the saddle of FIG. 11A.
Figure 11C:
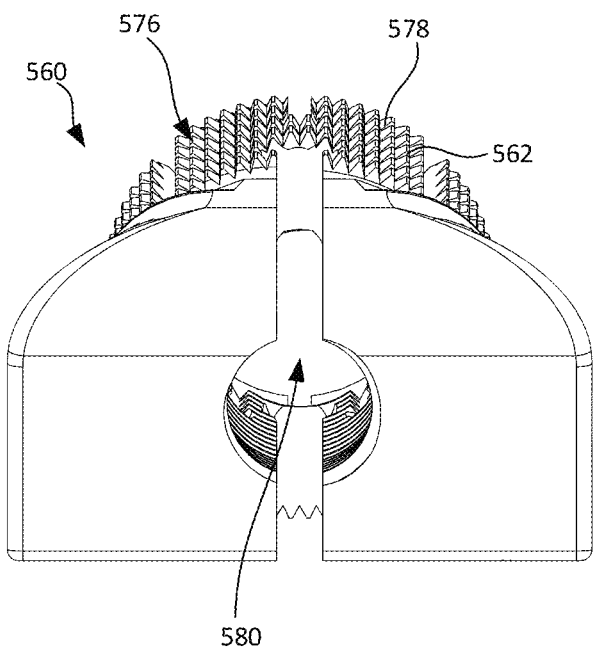
Figure 11D:
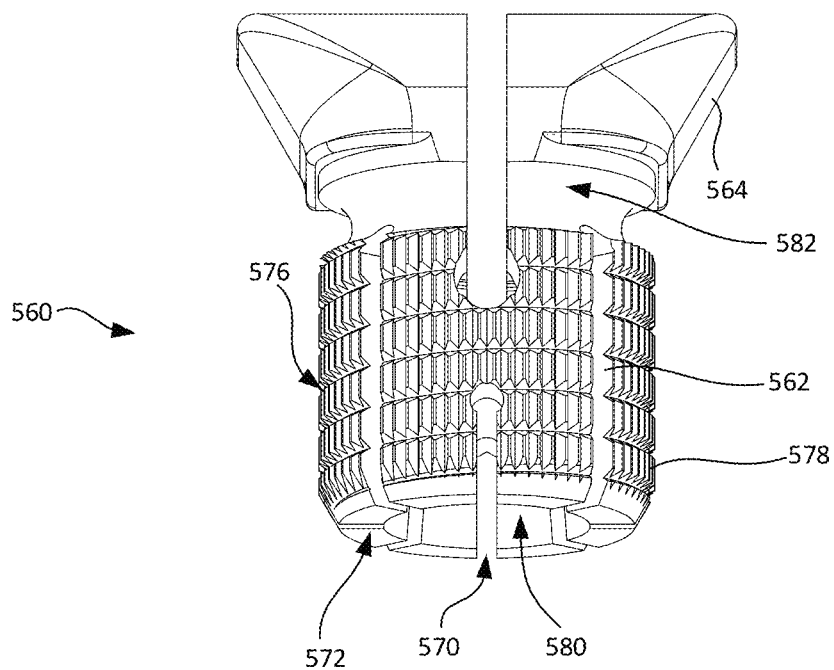
Figure 11E:
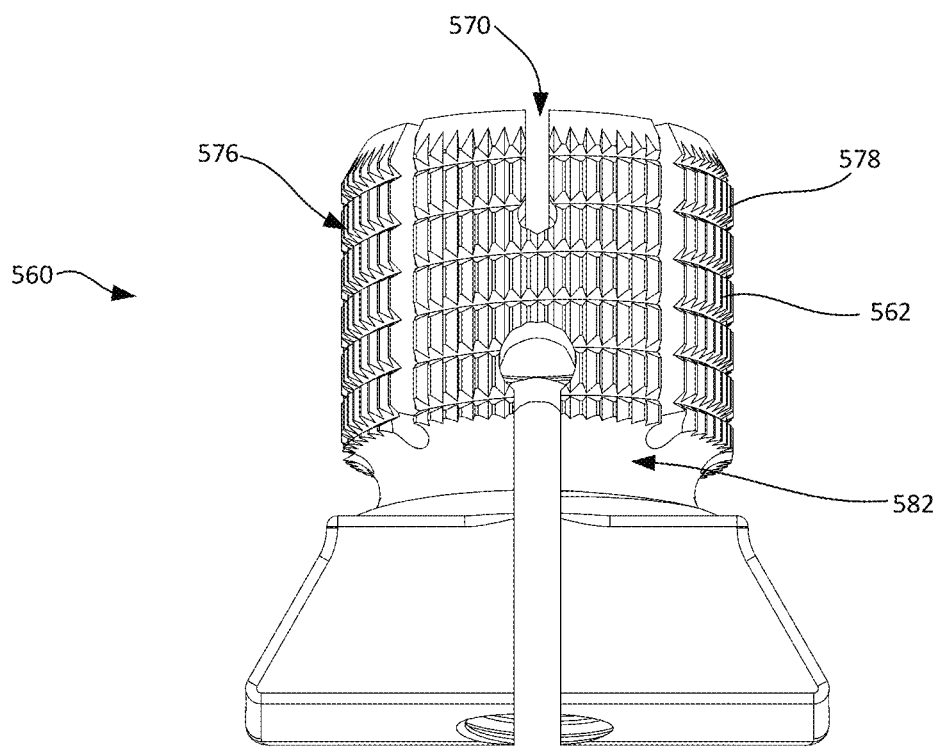
Figure 11F:
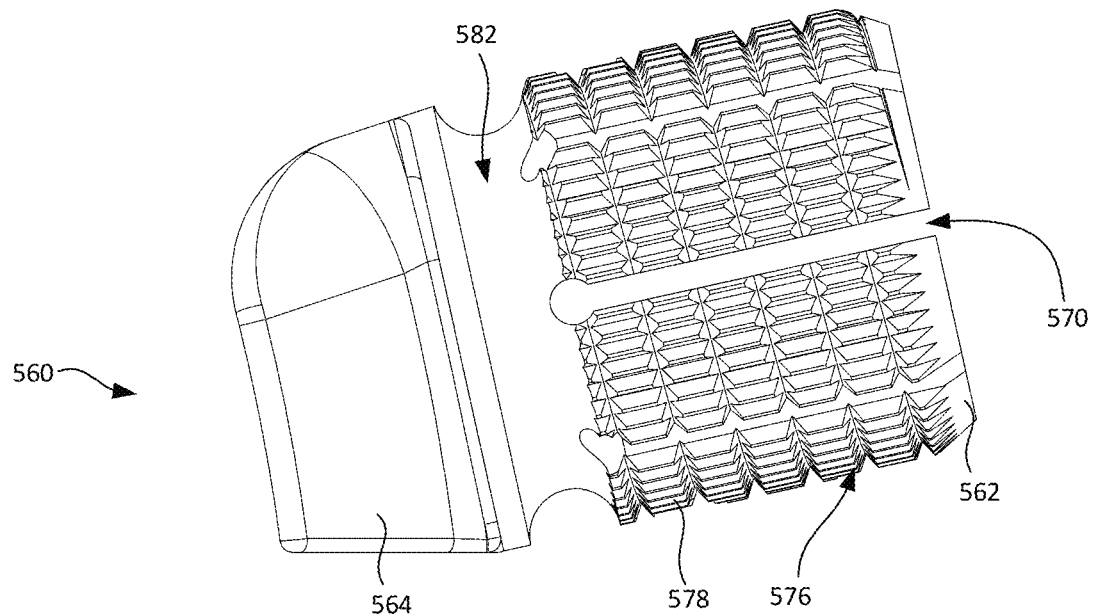
Figure 11G:
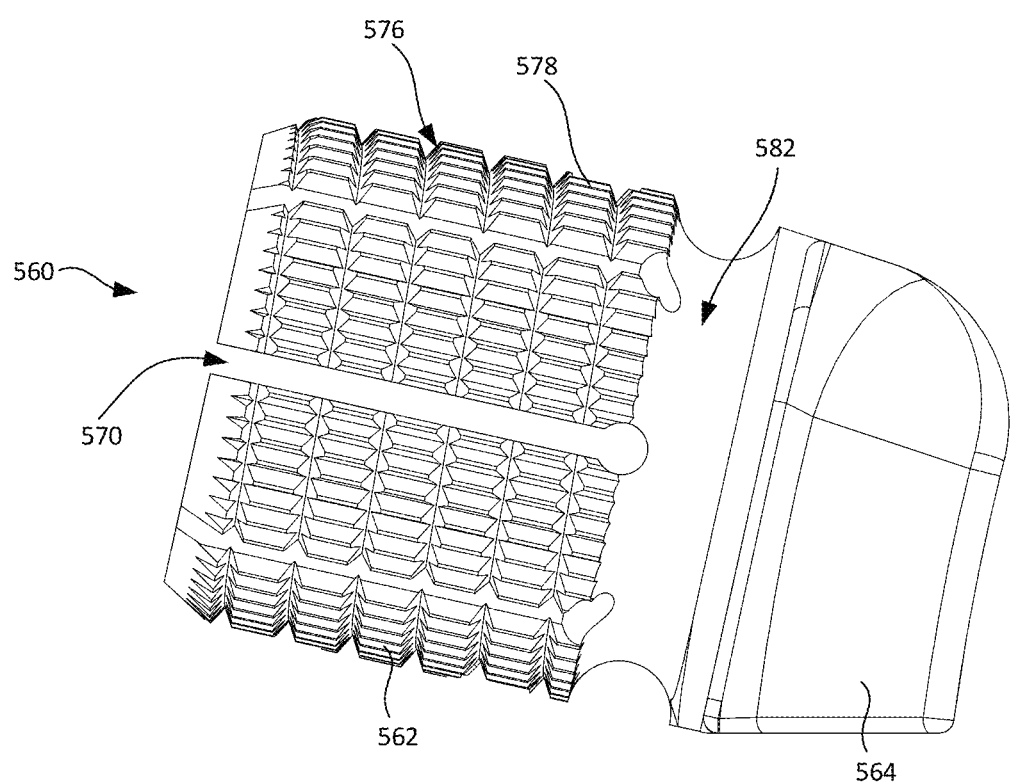

Referring now to FIGS. 10A-10C, the augment 504 can include a crescent-shaped flesh-facing surface 530, a cup-facing surface 532, and a bone-facing surface 534, all of which can be similar to corresponding surfaces of the augment 104 discussed above. However, the augment 504 can define a saddle hole 540 extending through the augment 504 from the augment bone-facing surface 534 to the augment cup-facing surface 532. The saddle hole 540 can generally become larger in steps as it extends from the augment bone-facing surface 534 to the augment cup-facing surface 532. The augment 504 can also define a pair of pin holes 542 extending into the augment 504 from the augment flesh-facing surface 530. The pin holes 542 can intersect the saddle hole 540, with pin holes passing through on opposing sides of the saddle hole 540.

The augment-securing mechanism 506 can include a lock ring 550 that can be seated against a shoulder in the saddle hole 540 in the augment 504. The saddle hole 540 can expand outward around the lock ring 550 to form an annular space (not shown) into which the lock ring 550 can expand. The augment-securing mechanism 506 can also include a pair of pins 552, such as spring pins that can be seated in the pin holes 542 in the augment 504.

A saddle 560 can be seated in the saddle hole 540. Referring to FIG. 9 and to FIGS. 11A-11G, the saddle 560 will now be described. The saddle 560 can include a generally cylindrical pivot or axle 562 and a generally dovetail-shaped slider 564. The axle 562 can define radial slots 570 that extend into the axle from a ring-facing surface 572 of the axle. The ring-facing surface 572 can face toward the lock ring 550 in the saddle hole 540 with the axle 562 being rotatable within the saddle hole 540 when the saddle 560 is in a non-expanded form. An outer surface 576 of the axle can define protrusions 578 that are configured to engage material of the augment 504 surrounding the saddle hole 540 when the saddle 560 is in an expanded form, with the portions of the axle separating so that the radial slots 570 widen. For example, the protrusions 578 can include multiple circumferentially-extending rows of axially-extending ridges. The axle 562 can define a rounded annular groove 582 that extends into the axle 562 from the outer surface 576. The annular groove 582 can align with the pin holes 542 so that the pins 552 are seated in the annular groove 582 on opposite sides of the axle 562, with the pins 552 inhibiting axial movement of the saddle 560 relative to the augment 504, but allowing rotational movement of the saddle 560 relative to the augment 504.

The slider 564 can extend from the axle 562, opposite the ring-facing surface 572. The slider 564 can be shaped similarly to the slider 140 discussed above, and can also function similarly to the slider 140 to expand and lock in place in the guide feature 124 of the cup 102. The saddle 560 can define a fastener hole 580 passing axially through the axle 562 and also through the slider 564. The fastener hole 580 can be internally threaded so that a threaded fastener 584 can be screwed into the fastener hole 580 and press outward on the axle 562 and the slider 564.

The augment-securing mechanism 506 and the augment-securing mechanism 170 may each be altered in various different ways in different embodiments. For example, the augment-securing mechanism 506 may be configured to allow the saddle to be expanded without accessing the bone-facing surface 534 of the augment 504. For example, the augment-securing mechanism 506 can include a pair of mating bevel gears. In such an embodiment, a rotating head at the flesh-facing surface 530 of the augment 504 can receive an instrument such as a bit of a bit driver. The head can be fixed to a first bevel gear (such as via a shaft). The first bevel gear can drive a second bevel gear, and that second bevel gear can drive a shaft that rotates to screw a fastener into the saddle 560. In one example, the shaft that screws the fastener may pass far enough into the fastener so that even as the fastener passes farther into the saddle, the shaft remains engaged in the fastener.

As another example, the guide feature may be formed in an augment and a slider may be located on the cup. Also, a guide feature may be a male feature and the slider may be a female feature. For example, the guide feature may be a rail formed along the cup, and the slider may be a feature attached to the augment that defines a slot into which the rail fits, allowing the augment to slide relative to the cup in the unlocked position. In such a configuration, a fastener may wedge into the rail to cause it to expand and lock the rail and slider together. Alternatively, a fastener may contract (squeeze) a female slider or guide feature so that it frictionally engages a male guide feature or slider, respectively.

Various manufacturing techniques and materials may be used for the components of the joint prostheses discussed herein, so long as the parts can be formed with sufficiently tight tolerances, and so long as the resulting parts exhibit traits normally considered for implanted prosthetics and for the functions discussed herein, such as sufficient strength, sufficient wear resistance, sufficient durability, and compatibility with the human body. For example, the components may be made of titanium. Also, for each of the components discussed herein, different manufacturing techniques may be used, such as 3D printing, machining, metal injection molding, and/or die casting. As an example, the cup and augment having the surface texture features illustrated in FIGS. 6A-7C may be formed by 3D printing.

The saddle 560 may be positioned in an augment 504 during manufacturing. Alternatively, the saddle 560 may be positioned in an augment 504 by a clinician prior to or during a surgical procedure to implant the joint prosthesis 500. Similarly, the augments for any of the embodiments can also be positioned on the cup by a clinician during a surgical procedure, although at least a portion of this may be performed prior to the surgical procedure.

Referring back to FIGS. 1-3G, in assembling the joint prosthesis 100, the fastener 172 can be screwed partially into the slider 140 without expanding the slider. The slider can be slid along a slot 126 in the cup 102, starting proximate the rim 120 of the cup and sliding until the augment 104 is moved to a desired position relative to the cup 102. At this time, the augment-securing mechanism can be actuated to secure the augment 104 to the cup 102 in this position. This can include moving the instrument 174 toward the cup in an access direction 600 (see FIG. 1). The access direction can be generally perpendicular to the plane 122 that is proximate the rim 120 of the cup 102 (see FIG. 2B). As used herein, generally perpendicular means within thirty degrees of being perpendicular. The instrument (174) can be used to screw the fastener 172 into the aperture 154 in the slider 140. This can include the fastener 172 rotating around an axis that is generally perpendicular to the plane 122. Also, the fastener can move in a direction that is generally perpendicular to the plane 122, from the joint side of the prosthesis 100. Actuation of the fastener 172 can expand the slider 140 into the expanded slider form, so that the slider frictionally engages the guide feature 124 along the slot 126, fixing the augment 104 in place relative to the cup 102. The joint prosthesis 200 and the joint prosthesis 300 can be assembled using similar techniques, with the augments being fixed in place relative to the cups in similar ways.

In assembling the joint prosthesis 500 of FIGS. 8-11G, the lock ring 550 can be seated in the saddle hole 540, and the saddle 560 can be moved into the saddle hole 540 from the augment cup-facing surface 532, with the ring-facing surface 572 extending in first, facing the lock ring 550. The pins 552 can then be pressed into the pin holes 542, to inhibit axial movement of the saddle 560. The fastener 584 can be partially screwed into the fastener hole 580 of the saddle 560 from the side of the augment bone-facing surface 534. The augment 504 can be moved so that the slider 564 slides into a slot 126 in the cup 102 proximate the rim 120. The augment 504 can be slid along the slot 126 and rotated relative to the saddle 560 until the augment 504 is in a desired position.

In that position, an instrument 174 can be used to actuate the fastener 584 by screwing the fastener into the saddle hole 540. The fastener 584 can press outward on the axle 562 and the slider 564 as it is being screwed into the fastener hole 580. This can cause the protrusions 578 on the axle 562 to frictionally engage the material around the saddle hole 540 and can cause the slider 564 to frictionally engage the guide feature 124 defining the corresponding slot 126 in which the slider 564 is seated. This can fix the saddle 560 in position relative to the augment 504 and relative to the cup 102, thereby fixing the augment 504 in position relative to the cup 102. As the fastener 584 is screwed into the saddle 560, a flared head of the fastener 584 can force the lock ring 550 to expand. When the head passes the lock ring 550, the lock ring 550 can contract due to its spring force. The lock ring 550 can then inhibit loosening of the fastener 584, and thus inhibit loosening of the augment 504 relative to the cup 102.

Portions of the assembly of the prosthesis may be performed by a clinician during a surgical procedure. For example, an acetabulum and an area around the acetabulum may be prepared during a surgical procedure, and an acetabular cup may be position and secured in the acetabulum. For example, the acetabular cup may be positioned by screwing a fastener through the cup and into the pelvis. The augment may then be moved and adjusted to a desired position, such as by sliding and/or rotating the augment as discussed above. An augment-securing mechanism may then be actuated to fix the augment in position relative to the already-positioned cup. Additional securing may then be performed, such as by screwing fasteners through the augment and into the pelvis.

Alternatively, a desired position of an augment relative to an acetabular cup may be determined, and the augment may be slid and/or rotated into place. The augment-securing mechanism can then be actuated to fix the augment in place relative the cup, prior to the cup being implanted. With the augment positioned relative to the cup, the assembled joint prosthesis can be positioned in the prepared acetabulum and secured in place relative to the pelvis, such as using fasteners screwed through the cup and/or the augment and into the pelvis.

For joint prostheses having multiple augments, one or more of the augments may be positioned and fixed relative to the cup before and/or after securing the cup in place in an acetabulum Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

The invention claimed is:

1. A system comprising:
    an acetabular cup comprising a first exterior surface comprising a first uneven texture defined by a first web of rods and first protrusions; and
    an augment securable to the acetabular cup, the augment comprising a second exterior surface comprising a second uneven texture defined by a second web of rods and second protrusions;
    wherein the first uneven texture and the second uneven texture are shaped such that, in response to pressure urging the acetabular cup and the augment together, the first protrusions enter interstitial spaces between the second web of rods and the second protrusions enter interstitial spaces between the first web of rods to interlock the augment with the acetabular cup.

2. The system of claim 1, further comprising an augment-securing mechanism configured to secure the acetabular cup to the augment.

3. The system of claim 1, wherein the rods of the first web of rods define a generally stochastic pattern.

4. The system of claim 1, wherein the second protrusions extend generally perpendicular to the second exterior surface.

5. A method comprising:
    Implanting a first implant comprising an acetabular cup comprising a first exterior surface comprising a first uneven texture defined by a first web of rods and first protrusions;
    Implanting a second implant comprising an augment securable to the acetabular cup, the augment comprising second exterior surface comprising a second uneven texture defined by a second web of rods and second protrusions; and
    pressing the first exterior surface against the second exterior surface such that the first protrusions enter interstitial spaces between the second web of rods and the second protrusions enter interstitial spaces between the first web of rods to interlock the augment with the acetabular cup.

6. The method of claim 5, further comprising actuating an augment-securing mechanism to secure the augment to the acetabular cup.

7. The method of claim 5, wherein the rods of the first web of rods define a generally stochastic pattern.

8. The method of claim 5, wherein the second protrusions extend generally perpendicular to the second exterior surface.

* * * * *